United States Patent
Baillet et al.

(10) Patent No.: US 9,801,806 B2
(45) Date of Patent: Oct. 31, 2017

(54) COMPOSITIONS FOR APPLICATION TO THE SKIN FOR REDUCING ADHESION OF POLLUTION PARTICLES ON SKIN AND METHODS OF PREPARING SAME

(71) Applicants: DOW CORNING CORPORATION, Midland, MI (US); DOW CORNING CHINA HOLDING CO., LTD., Shanghai (CN); DOW CORNING EUROPE S.A., Seneffe (BE)

(72) Inventors: Hortense Baillet, Le Havre (FR); Jean-Luc Garaud, Nivelles (FR); Lenin Petroff, Bay City, MI (US); Isabelle Van Reeth, Pudong (CN)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 15/110,805

(22) PCT Filed: Jan. 30, 2014

(86) PCT No.: PCT/CN2014/071846
§ 371 (c)(1),
(2) Date: Jul. 11, 2016

(87) PCT Pub. No.: WO2015/113307
PCT Pub. Date: Aug. 6, 2015

(65) Prior Publication Data
US 2016/0324757 A1 Nov. 10, 2016

(51) Int. Cl.
| *A61K 8/891* | (2006.01) |
| *A61K 8/34* | (2006.01) |
| *A61K 8/81* | (2006.01) |
| *A61K 8/04* | (2006.01) |
| *A61K 8/06* | (2006.01) |
| *A61K 8/41* | (2006.01) |
| *A61K 8/44* | (2006.01) |
| *A61K 8/37* | (2006.01) |
| *A61K 8/31* | (2006.01) |
| *A61Q 17/00* | (2006.01) |

(52) U.S. Cl.
CPC .............. *A61K 8/891* (2013.01); *A61K 8/042* (2013.01); *A61K 8/062* (2013.01); *A61K 8/064* (2013.01);
(Continued)

(58) Field of Classification Search
None
See application file for complete search history.

(56) References Cited

U.S. PATENT DOCUMENTS 6,500,470 B1   12/2002  Pauly
8,268,939 B2   9/2012  Ebbrecht et al.
(Continued)

FOREIGN PATENT DOCUMENTS

CN   101773460 A   7/2010
EP   2209462 B1   4/2013
(Continued)

*Primary Examiner* — Aradhana Sasan
(74) *Attorney, Agent, or Firm* — Catherine U. Brown

(57) ABSTRACT

Provided in various embodiments are compositions for topical application to the skin of a mammal, methods for their preparation, and their uses in skin care compositions to reduce adhesion of unwanted particles to the skin. When a hydrophobic non-volatile solvent and a hydrophobic non-volatile high melting point material with a melting point in the range of 60° C. and 100° C. are combined with a hydrophobic volatile solvent which compatibilizes the hydrophobic non-volatile solvent and the hydrophobic non-volatile high melting point material and the hydrophobic non-volatile high melting point material is selected to be at least partially incompatible with the hydrophobic non-volatile solvent in the absence of the hydrophobic volatile solvent, the resulting composition may be applied to skin to reduce adhesion of unwanted particles to the skin.

18 Claims, 1 Drawing Sheet

(52) U.S. Cl.
CPC ............... *A61K 8/31* (2013.01); *A61K 8/345* (2013.01); *A61K 8/37* (2013.01); *A61K 8/41* (2013.01); *A61K 8/44* (2013.01); *A61K 8/8152* (2013.01); *A61Q 17/00* (2013.01); *A61K 2800/805* (2013.01)

(56) References Cited

U.S. PATENT DOCUMENTS

| | | |
|---|---|---|
| 8,999,307 B2 | 4/2015 | Ranade et al. |
| 2002/0031533 A1 | 3/2002 | Afriat |
| 2002/0071820 A1 | 6/2002 | Afriat et al. |
| 2010/0266648 A1 | 10/2010 | Ranade et al. |
| 2011/0008401 A1 | 1/2011 | Ranade et al. |
| 2011/0104222 A1* | 5/2011 | Iida ................. A61K 8/375 424/401 |
| 2011/0117041 A1 | 5/2011 | Chantal et al. |
| 2012/0266648 A1 | 10/2012 | Berme et al. |
| 2012/0288462 A1 | 11/2012 | Lebok et al. |

FOREIGN PATENT DOCUMENTS

| | | |
|---|---|---|
| FR | 2836633 B1 | 8/2006 |
| JP | 2013095745 A | 5/2013 |
| KR | 20090046011 A | 5/2009 |

\* cited by examiner

COMPOSITIONS FOR APPLICATION TO THE SKIN FOR REDUCING ADHESION OF POLLUTION PARTICLES ON SKIN AND METHODS OF PREPARING SAME

CROSS-REFERENCE TO RELATED APPLICATIONS

This application is a U.S. national stage filing under 35 U.S.C. §371 of PCT Application No. PCT/CN14/071846 filed on Jan. 30, 2014, currently pending. PCT Application No. PCT/CN14/071846 is hereby incorporated by reference.

BRIEF SUMMARY OF THE INVENTION

The disclosure relates to compositions for topical application to the skin of a mammal, methods for their preparation, and their uses in skin care compositions to reduce adhesion of unwanted particles to the skin.

BRIEF DESCRIPTION OF THE DRAWINGS

The foregoing and other advantages of the invention will become apparent upon reading the following detailed description and upon reference to the drawings.

Figure 1:
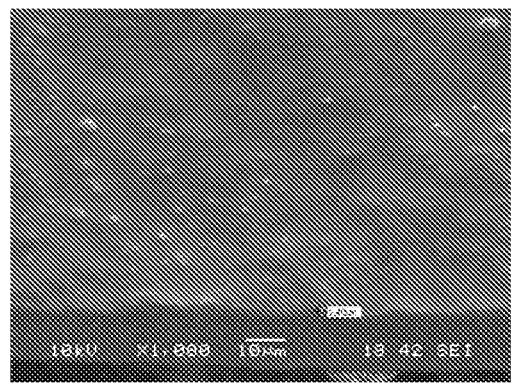
FIGS. 1, 2 and 3 are Scanning Electron Microscopy pictures of samples prepared and tested to evaluate adhesion levels of pollution particles onto collagen sheets.

While the invention is susceptible to various modifications and alternative forms, specific embodiments have been shown by way of example in the drawings and will be described in detail herein. It should be understood that the invention is not intended to be limited to the particular forms disclosed. Rather, the invention is to cover all modifications, equivalents, and alternatives falling within the spirit and scope of the invention.

DETAILED DESCRIPTION OF THE INVENTION

The present disclosure generally provides compositions and methods of making such compositions. The compositions of the present disclosure can be used in topical application to the skin to reduce adhesion of unwanted particles (such as pollutants, dirt, smoke, pollen, sand) to the skin.

It has been discovered that when a hydrophobic non-volatile solvent (component (a)) and a hydrophobic non-volatile high melting point material with a melting point in the range of 60° C. and 100° C. (component (b)) are combined with a hydrophobic volatile solvent (component (c)) which compatibilizes the hydrophobic non-volatile solvent and the hydrophobic non-volatile high melting point material and the hydrophobic non-volatile high melting point material is selected to be at least partially incompatible with the hydrophobic non-volatile solvent in the absence of the hydrophobic volatile solvent, the resulting composition may be applied to skin to reduce adhesion of unwanted particles to the skin. Upon application to the skin, the volatile solvent evaporates or vaporizes and the rest of the composition creates a film on the skin. This film is characterized by a specific micro-roughness on the nanometer/micrometer scale that minimizes the area of contact between the film and unwanted particles (such as pollutants, dirt, smoke, pollen, sand). The micro-roughened surface minimizes adhesion of the unwanted particles to the film, thereby potentially minimizing detrimental effects, such as pigment spots or extrinsic skin aging, when the unwanted particles come into contact with skin.

Features and advantages of the present disclosure will now be described with occasional reference to specific embodiments. However, the invention may be embodied in different forms and should not be construed as limited to the embodiments set forth herein. Rather, these embodiments are provided so that this disclosure will be thorough and complete and will fully convey the scope of the disclosure to those skilled in the art.

Unless otherwise indicated or defined, all technical and scientific terms used herein have the same meaning as commonly understood by one of ordinary skill in the art to which the invention pertains. The terminology used herein is for describing particular embodiments only and is not intended to be limiting. Accordingly, unless otherwise indicated, the numerical properties set forth in the specification and claims are approximations that may vary depending on the desired properties sought to be obtained in embodiments of the present disclosure. Notwithstanding that the numerical ranges and parameters setting forth the broad scope of the disclosure are approximations, the numerical values set forth in the specific examples are reported as precisely as possible. Any numerical values, however, inherently contain errors necessarily resulting from error found in their respective measurements. All percentages, parts, and ratios are based upon the total weight of the topical composition, unless otherwise specified. All such weights as they pertain to listed ingredients are based on the active level and, therefore, do not include carriers or by-products that may be included in commercially available materials, unless otherwise specified.

The compositions described herein are for topical application to skin of a mammal and include: (a) a hydrophobic non-volatile solvent (component (a)); (b) a hydrophobic non-volatile high melting point material, wherein the hydrophobic non-volatile high melting point material has a melting point in the range of 60° C. and 100° C. (component (b)); and (c) a hydrophobic volatile solvent (component (c)), wherein the hydrophobic volatile solvent (c) compatibilizes the hydrophobic non-volatile solvent (a) and the hydrophobic non-volatile high melting point material (b); and wherein the hydrophobic non-volatile high melting point material (b) is selected to be at least partially incompatible with the hydrophobic non-volatile solvent (a) in the absence of the hydrophobic volatile solvent (c).

The compositions optionally further include: (d) water (component (d)) and (e) one or more emulsifying systems (component (e)). The term "emulsifying system" is intended to be defined as any material or combination of materials capable of stabilizing an internal liquid phase as droplets into an external continuous liquid phase. The term "emulsifying system" is intended to cover a conventional emulsifier(s), a polymeric emulsifier(s) and/or any combination(s) thereof. Where water (d) and one or more emulsifying systems (e) are used, the compositions are in the form of an oil-in-water emulsion, a water-in-oil emulsion, or a hydrogel. When using water (d) and one or more emulsifying systems (e), the non-volatile high melting point material (b) is selected to be at least partially incompatible with the hydrophobic non-volatile solvent (a) and the one or more emulsifying systems (e) in the absence of the hydrophobic volatile solvent (c). The type and amount of each of components (a)-(e) used may be adjusted by one skilled in the art to arrive at a desired texture, product stability and skin feel for application to the skin, desired cosmetic effects, and based on consumer acceptability.

Hydrophobic Non-Volatile Solvent (Component (a))

Examples of suitable hydrophobic non-volatile solvents for use in embodiments of the invention include, but are not limited to, hydrocarbon oils of animal origin, hydrocarbon oils of vegetable origin, linear and branched hydrocarbons of mineral and synthetic origin, synthetic ethers comprising from 10 to 40 carbon atoms, synthetic esters, fatty alcohols that are liquid at ambient temperature and that comprise a branched and/or unsaturated carbon chain comprising from 12 to 26 carbon atoms, linear polydimethylsiloxanes, branched polydimethylsiloxanes, polydimethylsiloxanes substituted with fluoro, hydroxyl, thiol, amine, aliphatic (e.g., alkyl), aromatic (e.g., phenyl), polyoxyalkylene groups, fatty acids, fatty alcohols, sunfilters, and any combination(s) thereof. The hydrophobic non-volatile solvent has an oil-like consistency.

The hydrocarbon oils of vegetable origin include, but are not limited to, triglycerides comprising esters of fatty acids and glycerol, wherein the fatty acids can have various chain lengths ranging from $C_4$ to $C_{24}$, and wherein these chains may be linear or branched and saturated or unsaturated; triglycerides of heptanoic acid and triglycerides of octanoic acid; wheat germ, sunflower, grape seed, sesame, corn, apricot, castor, karite, avocado, olive, soybean, sweet almond, palm, rapeseed, cottonseed, hazelnut, macadamia, jojoba, alfalfa, poppy, pumpkinseed, cucumber, blackcurrant seed, evening primrose, millet, barley, quinoa, rye, safflower, candlenut, passionflower, and musk rose oil; karite butter; synthetic ethers comprising from 10 to 40 carbon atoms; triglycerides of caprylic/capric acids such as those sold by Stéarineries Dubois (Paris, France) and those sold under the names Miglyol® 810, 812, and 818 by Cremer Oleo (Hamburg, Germany), and their mixture(s).

The linear and branched hydrocarbons of mineral and synthetic origin include, but are not limited to, mineral oil, liquid petrolatum, polydecenes, hydrogenated polyisobutene such as Parleam® available from NOF Corporation (Tokyo, Japan), squalane, liquid paraffins, and their mixtures. The synthetic esters include, but are not limited to, oils of formula $R_1COOR_2$, wherein $R_1$ is chosen from linear and branched fatty acid radicals comprising from 1 to 40 carbon atoms and $R_2$ is chosen from hydrocarbon chains such as branched hydrocarbon chains comprising from 1 to 40 carbon atoms, where the sum of the carbon atoms in $R_1$ and $R_2$ is greater than or equal to 10; non-limiting examples of these esters include Purcellin Oil® available from Geneva Laboratories Limited (British Virgin Islands), cetearyl octanoate, isopropyl myristate, isopropyl palmitate, $C_{12}$ to $C_{15}$ alkyl benzoates such as the material sold as Crodamol AB by Croda International (Snaith, UK), hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, heptanoates, octanoates, decanoates, and ricinoleates of alcohols and of polyalcohols such as propylene glycol dioctanoate; hydroxylated esters such as isostearyl lactate, diisostearyl malate, and 2-octyidodecyl lactate; polyol esters and pentaerythritol esters, and their mixture(s).

The fatty alcohols are liquid at ambient temperature and include, but are not limited to, alcohols comprising a branched and/or unsaturated carbon chain comprising from 12 to 26 carbon atoms such as octyldodecanol, cetyl alcohol, cetearyl alcohol, isostearyl alcohol, oleyl alcohol, 2-hexyldecanol, 2-butyloctanol, and 2-undecylpentadecanol, and higher fatty acids such as oleic acid, linoleic acid, linolenic acid, and their mixture(s).

The linear polydimethylsiloxanes (PDMS) such as, but not limited to, materials sold by Dow Corning Corporation (Midland, Mich.) are liquid at room temperature and may be branched, may be substituted with fluoro groups, functional groups such as hydroxyl, thiol or amine groups, aliphatic (e.g., alkyl) groups or aromatic (e.g., phenyl) groups, which are pendent and/or at the end of a silicone chain, these groups each containing from 2 to 24 carbon atoms; phenylsilicones, for instance phenyltrimethicones such as those available from Dow Corning, phenyldimethicones, trimethyl pentaphenyl trisiloxane such as those available from Dow Corning, tetramethyl tetraphenyltrisiloxane, phenyl trimethylsiloxydiphenylsiloxanes, diphenyl dimethicones, diphenyl methyldiphenyl trisiloxanes, 2-phenylethyl trimethylsiloxysilicates, and their mixture(s). Other examples of silicone oils include, but are not limited to, polysiloxanes modified with fatty acids, fatty alcohols or polyoxyalkylenes, fluorosilicates, perfluoro oils, and their mixture(s). Also included are divinyldimethicone/dimethicone copolymers such as those available from Dow Corning.

Examples of sunfilters include, but are not limited to, p-aminobenzoic acid and aminobenzoic acid derivatives such as 4-dimethylaminobenzoic acid-2-ethyl-hexylester and cinnamic acid and its derivatives, 4-methoxycinnamic acid isoamyl ester and 3-benzyliden-boranan-2-one and benzyliden-bornan-2-one derivatives, 3-(4')-methylbenzyliden-boman-2-one, 3-(4-sulfo)benzylidenebornan-2-one, and salicylic acid derivatives, homosalate such as the material commercialized under the trade name Neo Heliopan® HMS by Symrise (Holzminden, Germany), ethylhexyl salicylate such as the material commercialized under the trade name Neo Heliopan® 303 by Symrise, 4-isopropylbenzylsalicylate, salicylic acid-2-ethylhexylester, 3,3,5-trimethylcyclohexylsalicylate, and 3-imidazole-4-yl-acrylic acid and its esters, 2-phenylenebenzimidazole-5-sulfonic acid, methylene bis-benzotriazolyl-tetramethylbutylphenol, 2-cyano-3, 3-diphenylacrylic acid, butyl-methoxydibenzoyl methane and benzophenone or benzophenone derivatives such as benzophenone-3, benzophenone-4, octocrylene such as the material commercialized under the trade name Neo Heliopan® OS by Symrise (Holzminden, Germany), and their mixture(s).

Hydrophobic Non-Volatile High Melting Point Material (Component (b))

The hydrophobic non-volatile high melting point materials are characterized by having an amorphous phase, a crystalline phase, or a combination of an amorphous phase and a crystalline phase at 25° C. and atmospheric pressure conditions. Examples of suitable hydrophobic non-volatile high melting point materials for use in embodiments of the invention include, but are not limited to, mineral waxes, petroleum waxes, animal waxes, vegetable waxes, hydrogenated oils, fatty acid esters, glycerides, synthetic waxes, hydrocarbon-based silicone waxes, hydrocarbon-based silicone resin waxes, fluorocarbon-containing waxes, synthetic polymers, silicone resins, and any combination(s) thereof.

Examples of mineral waxes for use in embodiments of the invention include, but are not limited to, ceresin wax, montan wax, ozokerite, and their mixture(s). Examples of petroleum waxes for use in embodiments of the invention include, but are not limited to, paraffin wax, microcrystalline wax, petroleum jelly, and their mixture(s). Examples of animal waxes for use in embodiments of the invention include, but are not limited to, beeswax and lanolin wax.

Examples of hydrogenated oils for use in embodiments of the invention include, but are not limited to, hydrogenated polydodecene, hydrogenated polyisobutene, hydrogenated vegetable oil, hydrogenated palm oil, hydrogenated palm oil and derivatives, hydrogenated castor oil and derivatives, hydrogenated jojoba oil, hydrogenated shea butter, hydrogenated shea oil, and their mixture(s). Examples of fatty acid esters and glycerides for use in embodiments of the invention include, but are not limited to, the glyceryl esters of higher fatty acids such as glyceryl monostearate, glyceryl distearate, glyceryl tristearate, palmitate esters of glycerol, C<18-36 triglycerides, glyceryl tribehenate, and their mixture(s).

Examples of vegetable waxes for use in embodiments of the invention include, but are not limited to, carnauba wax, candelilla wax, palm kernel wax, and their mixture(s). Examples of synthetic waxes for use in embodiments of the invention include, but are not limited to, polyethylene wax, PEG-modified beeswax, PEG-modified lanolin wax, PPG-modified lanolin wax, synthetic beeswax, synthetic candelilla wax, synthetic wax, dimethiconol beeswax, dimethicone PEG-8 beeswax, and their mixture(s). Examples of hydrocarbon-based silicone waxes for use in embodiments of the invention include, but are not limited to, $C_{30}$-$C_{45}$ alkyl methicone and $C_{30}$-$C_{45}$ olefin (MP>60° C.), Bis-PEG-18 methyl ethyl dimethyl silane, stearyl dimethicone, and their mixture(s). Examples of hydrocarbon-based silicone resin waxes for use in embodiments of the invention include, but are not limited to, $C_{30}$-$C_{45}$ alkyldimethylsilyl polypropylsilsesquioxane such as those available from Dow Corning. Examples of fluorocarbon-containing waxes for use in embodiments of the invention include, but are not limited to, perfluorononylethyl carboxy dimethicone derivatives such as materials sold under the Pecosil® FST product range from Phoenix Chemical Inc. (Somerville, N.J.), trifluoropropyldimethyl/trimethylsiloxysilicate, trifluoropropyldimethylsiloxy/trimethylsiloxy silsesquioxane, and their mixture(s). Examples of synthetic polymers for use in embodiments of the invention include, but are not limited to, radical polymers and polycondensation polymers, and their mixture(s). Non-limiting examples of radical polymers are acrylic polymers, acrylic acid copolymers, ethylene-vinyl acetate copolymers, and their mixture(s). Non-limiting examples of polycondensation polymers are anionic, cationic, nonionic or amphoteric polyurethanes, urethane/acrylic copolymers, urethane/polyvinyl pyrrolidone copolymers, ester/urethane copolymers, ether/urethane copolymers, urea/urethane copolymers, polyurea as well as polydimethylsiloxanes substituted with an organic group, and their mixture(s). Specifically included in the invention are acrylic copolymers with dendrimeric silicone groups such as those available from Dow Corning. Nonlimiting examples of silicone resins include trimethylsiloxysilicate, polypropylsilsesquioxane, polymethylsilsesquioxane vinyl dimethicone/methicone silsesquioxane crosspolymer, and their derivatives and mixture(s).

The hydrophobic non-volatile high melting point materials are generally in a wax-like state. In other words, the hydrophobic non-volatile high melting point materials are generally in a solid or semi-solid state.

In some embodiments, the hydrophobic non-volatile high melting point materials have a melting point in the range of 60° C. and 100° C. In some embodiments, the hydrophobic non-volatile high melting point materials have a melting point in the range of 60° C. and 90° C. In still further embodiments, the hydrophobic non-volatile high melting point materials have a melting point in the range of 60° C. and 80° C. In still further embodiments, the hydrophobic non-volatile high melting point materials have a melting point in the range of 60° C. and 70° C.

The hydrophobic non-volatile high melting point materials are characterized by having a high glass transition (Tg) temperature in the range of 60° C. and 100° C. In some embodiments, the hydrophobic non-volatile high melting point materials have a Tg in the range of 60° C. and 90° C. In still further embodiments, the hydrophobic non-volatile high melting point materials have a Tg in the range of 60° C. and 80° C. In still further embodiments, the hydrophobic non-volatile high melting point materials have a Tg in the range of 60° C. and 70° C.

The hydrophobic non-volatile high melting point materials are characterized by having a softening point in the range of 60° C. and 100° C. In some embodiments, the hydrophobic non-volatile high melting point materials have a softening point in the range of 60° C. and 90° C. In still further embodiments, the hydrophobic non-volatile high melting point materials have a softening point in the range of 60° C. and 80° C. In still further embodiments, the hydrophobic non-volatile high melting point materials have a softening point in the range of 60° C. and 70° C.

Hydrophobic Volatile Solvent (Component (c))

Examples of suitable hydrophobic volatile solvents for use in embodiments of the invention include, but are not limited to, volatile hydrocarbon oils comprising from 8 to 16 carbon atoms, volatile silicone oils, volatile fluorinated oils, and any combination(s) thereof. The hydrophobic volatile solvent compatibilizes the hydrophobic non-volatile solvent (a) and the hydrophobic non-volatile high melting point material (b). In other words, the hydrophobic volatile solvent assists with the mixing properties of components (a) and (b). Without the use of the hydrophobic volatile solvent (c), components (a) and (b) would phase separate.

The volatile hydrocarbon oils include, but are not limited to, hydrocarbon oils comprising from 8 to 16 carbon atoms, for example branched $C_8$-$C_{16}$ alkanes such as $C_8$-$C_{16}$ isoalkanes of petroleum origin (also referred to as isoparaffins), for instance isododecane (also referred to as 2,2,4,4,6-pentamethylheptane), isodecane, isohexadecane, and, for example, the oils sold under the trade names Isopar® and Permethyl® available The Presperse Corporation (Somerset, N.J.), and their mixture(s). Representative volatile oils include non-polar volatile hydrocarbon-based oils (which as used herein refers to oil containing only hydrogen and carbon atoms), silicone oils (optionally comprising alkyl or alkoxy groups that are pendant or at the end of a silicone chain), fluoro oils, and their mixture(s). Suitable hydrocarbon-based oils include isoparaffins, i.e., branched alkanes containing 8-16 carbon atoms such as isododecane (also known as 2,2,4,4,6-pentamethylheptane), petroleum distillates, and their mixture(s).

The volatile silicone oils include, but are not limited to, volatile linear and cyclic silicone oils, for instance those that have a viscosity of less than or equal to 5 centistokes ($5 \times 10^{-6}$ m$^2$/S) and that comprise, for example, from 2 to 10 silicon atoms such as from 2 to 7 silicon atoms, and their mixture(s). These silicones optionally comprise alkyl or alkoxy groups comprising from 1 to 10 carbon atoms. Further non-limiting examples are octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, caprylyl methicone, hexyl methicone, methyl trimethicone and their mixture(s).

The volatile fluorinated oils include, but are not limited to, perfluorocycloalkyls such as perfluoromethylcyclopentane and perfluoro-1,3-dimethylcyclohexane, perfluoroalkanes such as dodecafluoropentane and tetradecafluorohexane, heterofluoroalkyl or fluoroalkyl materials such as nonafluoromethoxybutane and perfluoromorpholine derivatives such as 4-trifluoromethylperfluoromorpholine, and their mixture(s).

At temperatures above 32° C., the hydrophobic volatile solvent evaporates or vaporizes when the composition is placed onto skin of a mammal. Once the hydrophobic volatile solvent evaporates or vaporizes, it is desirable that the hydrophobic volatile solvent not solubilize the non-volatile high melting point material.

The hydrophobic non-volatile high melting point material is selected to be at least partially incompatible with the hydrophobic non-volatile solvent in the absence of the hydrophobic volatile solvent. In other words, the non-volatile solvent (component (a)) and the non-volatile high melting point material (component (b)) are incompatible with one another once the non-volatile solvent (component (c)) has evaporated or vaporized. By "incompatible," this term is intended to mean that at least a fraction of the non-volatile phase turns into a solid form under standard conditions of temperature and pressure.

Water (Component (d))

The compositions described herein optionally include water. The water may be deionized water, mineral water, spring water, demineralized water, a floral water such as cornflower water, and their mixture(s). The water component main contain a variety of water-soluble ingredients of interest for cosmetic use such as a polyol which is miscible with water at ambient temperature (25° C.) chosen, for example, from polyols having from 2 to 20 carbon atoms (preferably having from 2 to 10 carbon atoms and preferentially having from 2 to 6 carbon atoms, such as glycerol, propylene glycol, butylene glycol, pentylene glycol, hexylene glycol, dipropylene glycol or diethylene glycol); and glycol ethers having from 3 to 16 carbon atoms, such as mono-, di- or tripropylene glycol ($C_1$-$C_4$) alkyl ethers, or mono-, di- or triethylene glycol ($C_1$-$C_4$) alkyl ethers; and their mixture(s). The water component may also contain a monoalcohol having from 2 to 6 carbon atoms such as ethanol or isopropanol.

Emulsifying System (Component (e))

As detailed above, the term "emulsifying system" is intended to cover a conventional emulsifier(s), a polymeric emulsifier(s) and/or any combination(s) thereof.

Examples of suitable emulsifying systems for use in embodiments of the invention include, but are not limited to, PEG, PEG/PPG or polyglycerin modified dimethicone, alkyldimethicone, dimethicone crosspolymer or Abn copolymer derivatives, fatty acid esters of polyols, polyoxyethylenated fatty acid esters (such as stearate or oleate) of sorbitol; polyoxyethylenated alkyl (such lauryl, cetyl, stearyl, or octyl) ethers, carboxylates (such as (sodium 2-(2-hydroxyalkyloxy)acetate))), amino acid derivatives (such as N-acylglutamates, N-acylgly-cinates, or acylsarcosinates), alkyl sulfates, alkyl ether sulfates and oxyethylenated derivatives thereof, sulfonates, isethionates, N-acylisethionates, taurates, N-acyl N-methyltaurates, sulfosuccinates, alkylsulfoacetates, phosphates, alkyl phosphates, polypeptides, anionic derivatives of alkyl polyglycoside (such as (acyl-D-galactoside uronate)), fatty acid soaps, polymeric o/w emulsifiers, and their mixture(s).

Conventional emulsifiers are surfactant molecules that have an amphiphilic molecular structure consisting of a polar (hydrophilic) and a non-polar (lipophilic) part, which are spatially separated from each other. Emulsifiers reduce the surface tension between the phases by being arranged at the interface between the two liquids. They form interfacial films at the oil/water phase interface which countervails the irreversible coalescence of the droplets. Conventional emulsifiers can be classified, based on the hydrophilic part of the molecule, into ionic (anionic, cationic and amphoteric) emulsifiers and non-ionic emulsifiers.

Examples of emulsifiers for preparing water-in-oil (W/O) emulsions include sorbitan, glycerol or sugar alkyl ester or ether derivatives such as the Dehymuls® range of products by BASF (Ludwigshafen, Germany), Hostacerin® DGI or Hostacerin® DGMS by Clariant International (Muttenz, Switzerland), sorbitan esters such as the Montane® range of products by Seppic (Paris, France); silicone surfactants, for instance PEG-10 dimethicone such as those available from Dow Corning, PEG/PPG-19/19 dimethicone such as those available from Dow Corning, PEG/PPG-18/18 dimethicone such as those available from Dow Corning, and alkyldimethicone copolyols such as laurylmethicone copolyols such as those available from Dow Corning; lauryl PEG-10 tris (trimethylsiloxy)silylethyl dimethicone such as those available from Dow Corning; cetyldimethicone copolyol such as the product sold under the name Abil® EM 90R by Evonik Industries (Essen, Germany), the mixture of cetyldimethicone copolyol, of polyglyceryl isostearate (4 mol) and of hexyl laurate, sold under the name Abil® WE O9 by Evonik Industries, bis-(glyceryl/lauryl) glyceryl lauryl dimethicone sold under the name Abil® EM 120 by Evonik Industries, polyether, polyether/alkyl or polyglycerin-modified linear, branched or cross-linked silicones from the KF range of products commercialized by Shin-Etsu Chemical (Tokyo, Japan), polyether-modified silicones from the Gransurf® range of products commercialized by Grant Industries (Elmwood Park, N.J.), ABn silicone polyethers such as PEG 14 Dimethicone Copolymer or PEG/PPG 10/7 Dimethicone Copolymer such as those available from Dow Corning and their mixture(s).

One or more co-emulsifiers may also be added thereto, which may be chosen from the group comprising polyol alkyl esters, glycerol and/or sorbitan esters, and their mixture(s). Examples of polyol alkyl esters include polyethylene glycol esters, for instance PEG-30 dipolyhydroxystearate, such as the product sold under the name Arlacel® P135 by Croda International. Examples of glycerol and/or sorbitan esters include polyglyceryl isostearate such as the product sold under the name Isolan® GI 34 by Evonik Industries, sorbitan isostearate such as the product sold under the name Arlacel® 987 by Croda International, sorbitan glyceryl isostearate such as the product sold under the name Arlacel® 986 by Croda International, and their mixture(s).

Examples of emulsifiers for preparing oil in water (O/W) emulsions include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters such as the mixture PEG-100 stearate/glyceryl stearate sold, for example, by INCI under the name Arlacel® 165 by Croda International; oxyalkylenated (oxyethylenated and/or oxypropylenated) fatty alkyl ethers; sugar esters such as sucrose stearate; fatty alkyl ethers of sugars including alkyl polyglucosides (APG) such as decylglucoside and laurylglucoside sold, for example, by Henkel (Dusseldorf, Germany) under the respective names Plantaren® 2000 and Plantaren® 1200, cetostearyl glucoside optionally as a mixture with cetostearyl alcohol, sold, for example, under the name Montanov® 68 by Seppic, under the name Tegocare CG90 by Evonik Industries and under the name Emulgade® KE3302 by Henkel, and also arachidyl glucoside, for example in the form of a mixture of arachidyl alcohol, behenyl alcohol and arachidyl glucoside, sold under the name Montanov® 202 by Seppic, and their mixture(s).

Polymeric o/w emulsifiers are polymers that are capable of stabilizing oil droplets in a water-based system without the use of monomeric surfactant emulsifiers. Polymeric o/w emulsifiers generally consist of a water soluble polymer backbone with pendant fatty groups. The fatty groups function similarly to the oil soluble portion of a conventional surfactant in that they interact with the oily material in an emulsion to help solubilize or compatibilize it with water, while the water soluble portion remains in solution in the water. Several types of polymeric o/w emulsifiers are available commercially. Anionic types include Pemulen® TR1 and TR2 and Carbopol® 1342, 1382, ETD 2020 Polymer, Ultrez 20 and Ultrez 21 products (acrylates C10-30 alkyl acrylates crosspolymer) by Lubrizol, the Simulgel® product range including Simulgel® 600 (mixture of polysorbate 80 and isohexadecane and acrylamide/sodium acryloyldimethyltaurate), the Sepigel product range including Sepigel 305® and Sepigel 501, and the Sepiplus and Sepinov product range, all available from Seppic, and their mixture(s). Other examples include the Aristoflex® product range (hydrophilic acrylic polymers) including Aristoflex® AVC (ammonium acryloyldimethyltaurate/VP copolymer) and Aristoflex® HMB by Clariant International, the acrylic polymers and cyanoacrylate Aculyn® products by Rohm and Haas (Philadelphia, Pa.), the mixture of sodium polyacrylate, dimethicone, cyclopentasiloxane, trideceth-6 and PEG/PPG-18/18 dimethicone available from Dow Corning, OptaSense® RMA 110 and OptaSense® RMA IS by Croda International, the FlexiThix® and Rapithix® products by Ashland, Inc. (Covington, Ky.), the Salcare® and Tinovis® range of products from BASF (Ludwigshafen, Germany, alkyl modified hydroxyethyl cellulose such as Natrosol® Plus CS (cetyl hydroxyethyl cellulose) by Ashland and their mixture(s).

Optional Additional Ingredients

The compositions described herein may include one or more ingredients suitable or beneficial to the skin such as emollients and humectants and active ingredients for a specific targeted benefit such as exfoliate agents, vitamins, vitamin derivatives, sunscreens, fragrances, and their mixture(s). These ingredients can be incorporated into the composition at levels appropriate for a particular skin care application as determined by one of ordinary skill in the art.

The composition according to the present disclosure may include one or more ingredients including, but not limited to, humectants, emollients, exfoliate agents, vitamins and their derivatives, natural extracts and their derivatives, anti-oxidants, radical scavengers, anti-acne agents, anti-inflammatory agents, antimicrobial agents, antibacterial agents, antifungal agents, anti-itch agents, peptides, proteins, sunscreens, sunfilters, skin lightening agents, tanning agents, drugs, pigments, dyes, electrolytes, sequestrants, anhydrous liquids, thickeners/rheology modifiers, preservatives, fragrances, pH modifiers, and combination(s) thereof. Examples of electrolytes include sodium chloride. Examples of sequestrants include ethylene diamine tetra-acetate salts. Examples of preservatives include phenoxyethanol, ethylhexylglycerin, diazolidinyl urea, iodopropynyl butylcarbamate, potassium sorbate, and their mixture(s). Examples of pH modifiers include citric acid, lactic acid, sodium hydroxide, triethanolamine or aminomethyl propanol, and their mixture(s).

Process

As described above, once the inventive compositions are applied to the skin, the hydrophobic volatile solvent evaporates or vaporizes to form a film on the skin. While not desiring to be bound by particular theories, it is believed that when the hydrophobic volatile solvent evaporates or vaporizes, the hydrophobic non-volatile high melting point material, by virtue of being partially incompatible with the rest of the non-volatile phase, undergoes a solidification process that generates some level of surface micro-roughness. When the film is formed on the skin (or a collagen sheet), the film has a specific micro-roughness characterized on the nanometer/micrometer scale. The film also has a non-smooth surface. The micro-roughness is defined as a surface that is not visibly smooth when observed using scanning electromicroscopy at magnification ×1,000. The micro-roughened surface minimizes adhesion of unwanted particles (such as pollutants, dirt, smoke, pollen, sand) to the film, thereby minimizing detrimental effects when the unwanted particles come into contact with skin. The presence of the micro-roughened surface is expected to limit the detrimental oxidative effects on skin (e.g., accelerated aging) caused by exposure to the pollution particles and the other types of unwanted particles.

Routes to create micro-roughness at the desired nanometer/micrometer scale on a substrate have been described in the literature. Surface-treating products claiming a lotus-like effect (that is, having micro-roughness) are available commercially; however, those surface-treating products typically use solid particulates to create the required micro-roughness. Solid particulates are particulates that are not able to fully dissolve into any phase of the composition at standard conditions (25° C. and atmospheric pressure). Solid particulates are applied onto the substrate to treat and then remain entrapped into a thin film of matrix or binder, thus forming surface irregularities. Depending on the application, the commercially available surface-treating products claiming a lotus-like effect may or may not be diluted. One constraint of such products is that they are sensitive to dilution since the micro-roughness density is driven by the solid particulate density ultimately obtained on the substrate. Since those solid particulates cannot dissolve into any phase of the composition before application on the substrate, consumer acceptability related to sensory or product aspect may be greatly degraded, given the high solid particulate content required in the composition. Commercial examples of such materials outside personal care applications are Tegotop® 210 available from Evonik Industries and the Sto Lotusan® product range available from Sto S.A.S. (Schiltigheim, France).

The present disclosure also relates to a method of preparing a composition for topical application to the skin of a mammal, including the steps of mixing the hydrophobic non-volatile solvent (a) with the hydrophobic non-volatile high melting point material (b), wherein the hydrophobic non-volatile high melting point material has a melting point in the range of 60° C. and 100° C. and with the hydrophobic volatile solvent (c). The hydrophobic volatile solvent compatibilizes the hydrophobic non-volatile solvent and the hydrophobic non-volatile high melting point material and the hydrophobic non-volatile high melting point material is selected to be at least partially incompatible with the hydrophobic non-volatile solvent in the absence of the hydrophobic volatile solvent.

The inventive methods further involve mixing (d) water and (e) one or more emulsifying systems with the hydrophobic non-volatile solvent, the hydrophobic non-volatile high melting point material, and the hydrophobic volatile solvent into an oil-in-water emulsion, a water-in-oil emulsion, or a hydrogel. Where water (d) and one or more emulsifying systems (e) are additionally used, the non-volatile high melting point material is selected to be at least partially incompatible with the hydrophobic non-volatile solvent and the one or more emulsifying systems in the absence of the hydrophobic volatile solvent.

The compositions described herein may be used in skin care or cosmetic products in various forms selected from lotions, creams, moisturizers, facial treatments, primers, concealers, foundations, make-ups, color cosmetics, blushes, lipsticks, lip balms, eyeliners, powders, and sunscreens.

Micro-Roughness Effect

Creating a micro-roughened surface on a substrate that ultimately leads to minimizing particle adhesion onto a substrate has been widely described. Prior solutions typically use solid particulates to create the micro-roughened surface. It has surprisingly been discovered that a micro-roughened surface leading to pollution particle anti-adhesion could be delivered from a cosmetic formulation through a process of high melting point material recrystallization, the recrystallization being induced by a partial or total incompatibility between the high melting point material and the rest of the non-volatile phase ingredients.

The inventive compositions are configured to provide a micro-roughness effect. The adhesion level between two materials generally depends on the chemical interaction of the materials and the area of contact between the materials. The chemical interaction is driven by the respective chemical nature of the materials. The area of contact results from the respective surface topography of the materials. Micro-roughness can be described as having a peak-and-valley pattern when viewed under magnification such as using Scanning Electron Microscopy tooling. Where no peaks or valleys are visible and the surface is smooth, there is a large area of contact between the film and unwanted particle(s). In this scenario, there are no microspaces. As a consequence, high adhesion is observed and unwanted particle(s) tend to stay in contact with the substrate. In the case of skin, this results in potential detrimental effects due to the action of, for example, polycyclic aromatic hydrocarbons or heavy metals adsorbed on unwanted particles. Where the peaks are separated from one another by large distances (i.e., order of magnitude of 10 microns or larger), the valleys (the inter-peak spaces) are large enough for unwanted particle(s) to fit into the inter-peak spaces and adhere to the film. In this scenario, the microspaces have a large enough size to allow unwanted particles to develop a large area of contact with the substrate, with similar negative consequences as the previously described scenario. Where the peaks are separated from one another by a smaller distance (i.e., order of magnitude of 1 micron or smaller), the valleys (the inter-peak spaces) are too small to provide space for unwanted particle(s) to fit into the inter-peak spaces and adhere to the film. As a consequence, the area of contact for the unwanted particle(s) is limited to the top of the peaks; the smaller area of contact leads to a reduction in adhesion and much fewer particles tend to stay in contact with the substrate. This potentially minimizes the negative effects derived from the contact of unwanted particles with skin. In this scenario, the microspaces have the appropriate size to prevent unwanted particles from developing a large enough area of contact with the substrate so that significant adhesion is observed.

A number of advantages are observed with the inventive compositions and methods described herein. First, the inventive compositions and methods solve the problem of particulate concentration limit that would be required to deliver a high enough particulate density on the desired substrate so that the anti-adhesion effect can be obtained. Particulates such as silica can have, especially at the high levels required to obtain an anti-adhesion effect, have a detrimental sensory impact; the inventive compositions and methods, however, provide for a more desirable aesthetic product without a detrimental sensory impact. In addition, the inventive compositions and methods avoid the potential instability issues associated with possible sedimentation of particulates in a cosmetic system. Further, the inventive compositions and methods avoid the typical visible (e.g., white) effect on skin resulting from the presence of high levels of larger than nanometric-size particulates in the composition. Additionally, the inventive compositions and methods avoid the need to use nano-sized particulates, which limits the toxicological impact of the inventive compositions.

EXAMPLES

These examples are intended to illustrate the invention to one of ordinary skill in the art and should not be interpreted as limiting the scope of the invention set forth in the claims. All parts and percentages in the examples are on a weight basis and all measurements were indicated at about 23° C. (room temperature), unless indicated to the contrary.

Table 1 below shows the list of ingredients used in the examples.

TABLE 1

| INCI Name | Supplier | Ingredient |
| --- | --- | --- |
| Glyceryl Stearate and PEG-100 stearate | Croda International (Snaith, UK) | 1 |
| Beeswax | Baerlocher (Unterschleissheim Germany) | 2 |
| Cetearyl alcohol | BASF (Ludwigshafen, Germany) | 3 |
| Isododecane | Presperse Corporation (Somerset, NJ) | 4 |
| $C_{12}$ to $C_{15}$ Alkyl Benzoate | Croda International (Snaith, UK) | 5 |
| Disodium EDTA | AkzoNobel (Amsterdam, The Netherlands) | 6 |
| Lauryl PEG-10 tris(trimethylsiloxy)silylethyl dimethicone | Dow Corning Corporation (Midland, MI) | 7 |
| Isododecane and polypropylsilsesquioxane | Dow Corning Corporation (Midland, MI) | 8 |
| Isododecane and acrylates/polytrimethylsiloxymethacrylate copolymer | Dow Corning Corporation (Midland, MI) | 9 |

TABLE 1-continued

| INCI Name | Supplier | Ingredient |
|---|---|---|
| Dimethicone and acrylates/polytrimethylsiloxymethacrylate copolymer | Dow Corning Corporation (Midland, MI) | 10 |
| Caprylyl methicone | Dow Corning Corporation (Midland, MI) | 11 |
| Divinyldimethicone/Dimethicone copolymer and $C_{12}$-$C_{13}$ pareth-23 and $C_{12}$-$C_{13}$ pareth-23 | Dow Corning Corporation (Midland, MI) | 12 |
| Trimethylsiloxysilicate | Dow Corning Corporation (Midland, MI) | 13 |
| Trimethylsiloxysilicate and polypropylsilsesquioxane | Dow Corning Corporation (Midland, MI) | 14 |
| Sodium polyacrylate and dimethicone and clclypentasiloxane and tri-deceth-6 and PEG/PPG-18/18 dimethicone | Dow Corning Corporation (Midland, MI) | 15 |
| $C_{30}$-$C_{45}$ Alkyldimethylsilyl polypropylsilsesquioxane | Dow Corning Corporation (Midland, MI) | 16 |
| Phenoxyethanol and ethylhexylglycerin | Schülke & Mayr GmbH (Norderstedt, Germany) | 17 |
| Glycerine | Rita Corporation (Crystal Lake, IL) | 18 |
| Diazolidinyl urea and iodopropynyl butylcarbamate | Ashland, Inc. (Covington, KY) | 19 |
| Mineral oil | Calumet Penreco (Karns City, PA) | 20 |
| Octocrylene | Symrise (Holzminden, Germany) | 21 |
| Homosalate | Symrise (Holzminden, Germany) | 22 |
| Ethylhexyl salicylate | Symrise (Holzminden, Germany) | 23 |
| Polyacrylamide and $C_{13}$-$C_{14}$ Isoparaffin and Laureth-7 | Seppic (Paris, France) | 24 |
| Propylene glycol | Rita Corporation (Crystal Lake, IL) | 25 |
| Candelilla wax | Rita Corporation (Crystal Lake, IL) | 26 |
| Sodium Chloride | | 27 |
| Triethanolamine | BASF (Ludwigshafen, Germany) | 28 |
| Acrylates/C10-30 alkyl acrylate crosspolymer | Lubrizol (Wickliffe, OH) | 29 |
| Water | | 30 |
| Dimethicone | Dow Corning Corporation (Midland, MI) | 31 |
| Dimethicone | Dow Corning Corporation (Midland, MI) | 32 |

Example 1: Preparation of Cream-Gel

Formulations in Samples 1-3 were prepared according to the following procedure. The amounts (quantity percentages) used for each sample are specified in Table 2 below.

Step 1:

Ingredient 29 was sprinkled in Ingredient 30 at room temperature and mixed well until homogeneous. A vortex was maintained above the stirrer and Ingredient 29 was sprinkled very gradually inside the vortex. Ingredient 6 was added while mixing until uniform. The stirring speed was increased (1000 rpm) as the neutralization step increases viscosity. Ingredient 28 (at 85%) was added drop-by-drop to adjust the pH to 5.5.

Step 2:

The stirring speed was reduced and Ingredient 30 and Ingredient 18 were added. Mixing was continued until uniform.

Step 3:

The Phase C ingredients were added quickly with a pipette under high mixing. The pH was adjusted to 5.5 as necessary with triethanolamine (at 85%).

Step 4:

A premix of propylene glycol (Ingredient 25) with preservative (Ingredient 19) was added while mixing. Mixing was maintained until uniform cream-gels were formed.

TABLE 2

| Ingredient Name | Ingredient | Sample 1 (Quantity %) | Sample 2 (Quantity %) | Sample 3 (Quantity %) |
|---|---|---|---|---|
| Phase A | | | | |
| Water | 30 | 75.56 | 75.56 | 75.56 |
| Acrylates/C10-30 alkyl acrylate crosspolymer | 29 | 0.5 | 0.5 | 0.5 |
| Disodium EDTA | 6 | 0.05 | 0.05 | 0.05 |
| Triethanolamine | 28 | 0.3 | 0.3 | 0.3 |
| Phase B | | | | |
| Water | 30 | 10.29 | 0.29 | 0.29 |
| Glycerine | 18 | 5 | 5 | 5 |
| Phase C | | | | |
| Isododecane and polypropylsilsesquioxane | 8 | — | — | — |
| Isododecane | 4 | — | — | 8.05 |
| Isododecane and acrylates/polytrimethylsiloxymethacrylate copolymer | 9 | — | 5 | — |
| Dimethicone | 31 | — | 5 | — |
| $C_{30}$-$C_{45}$ Alkyldimethylsilyl polypropylsilsesquioxane | 16 | — | — | 1.95 |
| Mineral oil | 20 | 3 | 3 | 3 |
| $C_{12}$-$C_{15}$ Alkyl Benzoate | 5 | 3 | 3 | 3 |
| Triethanolamine | 28 | 0.3 | 0.3 | 0.3 |

TABLE 2-continued

| Ingredient Name | Ingredient | Sample 1 (Quantity %) | Sample 2 (Quantity %) | Sample 3 (Quantity %) |
|---|---|---|---|---|
| Phase D | | | | |
| Diazolidinyl urea and iodopropynyl butylcarbamate | 19 | 0.5 | 0.5 | 0.5 |
| Propylene Glycol | 25 | 1.5 | 1.5 | 1.5 |
| | | 100 | 100 | 100 |
| Adhesion level (1 = low, 3 = high) | | 2 | 1 | 2 |

Particle adhesion was assessed in the following manner: A collagen sheet commercialized by the company Dera (Bornem, Belgium) was cut to the dimension and fixed by means of adhesive tape on a rectangular aluminum plate (size=7.5 cm by 15.1 cm). Creams were coated using a rod to push a quadruple applicator from Elcometer (Hermalle-sous-Argentau, Belgium) onto the collagen sheet with a speed corresponding to position 2 on a K Control Coater coating table from RK Printcoat Instrument Ltd (Royston, UK). Coating thickness was set to 60 microns. Films were then allowed to dry at room temperature for 24 hours.

Particle adhesion was then assessed using the following protocol: A 4.5×4.5 cm area of interest was exposed to carbon black in excess (~2 g) sprinkling the particles above the coating. Carbon black particles should cover the entire area of interest. Non-adherent carbon black was removed by turning the aluminum panel upside down. Pictures were then taken using the following settings: ISO 200, Focal length: 35 mm, Mode: Monochrome, Opening: f/7.1, Speed: 1/125 s, No flash, No exposure compensation, No timer. The camera used was a Canon Rebel T1i equipped with a EF-S 18-55 mm objective, both from Canon (Tokyo, Japan). The carbon black grade used was Black Pearls® 490 from Cabot (Boston, Mass.). In some cases, scanning electron microscopy images of the surfaces after coating on collagen but before exposure to carbon black were taken.

Adhesion was measured using a visual rating based on the quantity of particle remaining on the substrate. A rating of 1 corresponds to low particle adhesion. A rating of 2 corresponds to medium particle adhesion. A rating of 3 corresponds to high particle adhesion. The adhesion level of Sample 1 was rated at 2, Sample 2 was rated at 1, and Sample 3 was rated at 2. The results generally demonstrate that in the cream-gel chassis, using Ingredient 9 at a ~2% level reduced carbon black particle adhesion compared to the control without any high melting point material (Sample 1) or another high melting point material (Sample 3).

Example 2: Preparation of Oil-In-Water Emulsion

Formulations in Samples 4-15 were prepared according to the following procedure. The amounts (quantity percentages) used for each sample are specified in Tables 3a-3b below.

Step 1:
The Phase C ingredients were mixed under moderate mixing and heat to 85° C.

Step 2:
The Phase A ingredients were mixed and heated to 85° C. Mixing was continued until the ingredients were completely melted.

Step 3:
The Phase C mixture was added to the Phase A mixture.

Step 4:
The Phase D ingredients were mixed. The Phase D mixture was added to the combined phase C/phase A mixture with strong agitation.

Step 5:
The heating was discontinued. The Phase B ingredients were added to the previous system at a temperature at or below 38° C.

Step 6:
The Phase E ingredients were added to the previous system. Mixing was conducted until uniform oil-in-water emulsions were formed.

TABLE 3a

| Ingredient Name | Ingredient | Sample 4 (Control Formula) (Quantity %) | Sample 5 (Ingredient 9) (Quantity %) | Sample 6 (Ingredient 10) (Quantity %) | Sample 7 (Ingredient 14) (Quantity %) | Sample 8 (Ingredient 13) (Quantity %) | Sample 9 (Ingredient 8) (Quantity %) |
|---|---|---|---|---|---|---|---|
| Phase A | | | | | | | |
| Glyceryl stearate and PEG-100 stearate | 1 | 2 | 2 | 2 | 2 | 2 | 2 |
| Cetearyl alcohol | 3 | 0.5 | 0.5 | 0.5 | 0.5 | 0.5 | 0.5 |
| Mineral oil | 20 | — | — | — | — | — | — |
| Caprylyl methicone | 11 | — | — | — | — | — | — |
| $C_{12}$ to $C_{15}$ Alkyl Benzoate | 5 | 4.83 | 2.88 | 1.38 | 2.88 | 2.88 | 2.88 |
| Phase B | | | | | | | |
| Dimethicone | 31 | — | — | — | — | — | — |
| Isododecane | 4 | 3.05 | — | — | 3.05 | 3.05 | 2.4 |
| Dimethicone | 32 | — | — | — | — | — | — |
| Dimethicone and acrylates/polytrimethylsiloxymethacrylate copolymer | 10 | — | — | 6.5 | — | — | — |
| Trimethylsiloxysilicate and polypropylsilsesquioxane | 14 | — | — | — | 1.95 | — | — |
| Trimethylsiloxysilicate | 13 | — | — | — | — | 1.95 | — |

TABLE 3a-continued

| Ingredient Name | Ingredient | Sample 4 (Control Formula) (Quantity %) | Sample 5 (Ingredient 9) (Quantity %) | Sample 6 (Ingredient 10) (Quantity %) | Sample 7 (Ingredient 14) (Quantity %) | Sample 8 (Ingredient 13) (Quantity %) | Sample 9 (Ingredient 8) (Quantity %) |
|---|---|---|---|---|---|---|---|
| Isododecane and acrylates/polytrimethylsiloxymethacrylate copolymer | 9 | — | 5 | — | — | — | — |
| Isododecane and polypropylsilsesquioxane | 8 | — | — | — | — | — | 2.6 |
| $C_{30}$-$C_{45}$ Alkyldimethylsilyl polypropylsilsesquioxane | 16 | — | — | — | — | — | — |
| Phase C | | | | | | | |
| Octocrylene | 21 | 2.08 | 2.08 | 2.08 | 2.08 | 2.08 | 2.08 |
| Homosalate | 22 | 2.92 | 2.92 | 2.92 | 2.92 | 2.92 | 2.92 |
| Ethylhexyl salicylate | 23 | 2.08 | 2.08 | 2.08 | 2.08 | 2.08 | 2.08 |
| Phase D | | | | | | | |
| Polyacrylamide and $C_{13}$-$C_{14}$ Isoparaffin and Laureth-7 | 24 | 1.5 | 1.5 | 1.5 | 1.5 | 1.5 | 1.5 |
| Disodium EDTA | 6 | 0.1 | 0.1 | 0.1 | 0.1 | 0.1 | 0.1 |
| Water | | 75.1 | 75.1 | 75.1 | 75.1 | 75.1 | 75.1 |
| Glycerine | 18 | 5 | 5 | 5 | 5 | 5 | 5 |
| Phase E | | | | | | | |
| Phenoxyethanol and ethylhexylglycerin | 17 | 0.8 | 0.8 | 0.8 | 0.8 | 0.8 | 0.8 |
| | | 100.0 | 100.0 | 100.0 | 100.0 | 100.0 | 100.0 |
| Adhesion level (1 = low, 3 = high) | | 2 | 2 | 2 | 2 | 2 | 2 |

TABLE 3b

| Ingredient Name | Ingredient | Sample 10 (Ingredient 31) (Quantity %) | Sample 11 (Ingredient 16) (Quantity %) | Sample 12 (Ingredient 12) (Quantity %) | Sample 13 (Glycofilm) (Quantity %) | Sample 14 (Candelilla wax) (Quantity %) | Sample 15 (Beeswax) (Quantity %) |
|---|---|---|---|---|---|---|---|
| Phase A | | | | | | | |
| Glyceryl stearate and PEG-100 stearate | 1 | 2 | 2 | 2 | 2 | 2 | 2 |
| Cetearyl alcohol | 3 | 0.5 | 0.5 | 0.5 | 0.5 | 0.5 | 0.5 |
| Mineral oil | 20 | — | — | — | — | — | — |
| Caprylyl methicone | 11 | — | — | — | — | — | — |
| $C_{12}$ to $C_{15}$ Alkyl Benzoate | 5 | 2.88 | 2.88 | 2.88 | 2.88 | 2.88 | 2.88 |
| Phase B | | | | | | | |
| Dimethicone | 31 | — | — | — | — | — | — |
| Isododecane | 4 | 3.05 | 3.05 | 1.75 | 2 | 3.05 | 3.05 |
| Dimethicone | 32 | 1.95 | — | — | — | — | — |
| Dimethicone and acrylates/polytrimethylsiloxymethacrylate copolymer | 10 | — | — | — | — | — | — |
| Trimethylsiloxysilicate and polypropylsilsesquioxane | 14 | — | — | — | — | — | — |
| Trimethylsiloxysilicate | 13 | — | — | — | — | — | — |
| Isododecane and acrylates/polytrimethylsiloxymethacrylate copolymer | 9 | — | — | — | — | — | — |
| Isododecane and polypropylsilsesquioxane | 8 | — | — | — | — | — | — |
| $C_{30}$-$C_{45}$ Alkyldimethylsilyl polypropylsilsesquioxane | 16 | — | 1.95 | — | — | — | — |
| Divinyldimethicone/Dimethicone copolymer and $C_{12}$-$C_{13}$ pareth-23 and $C_{12}$-$C_{13}$ pareth-23 | 12 | — | — | 3.25 | — | — | — |
| Rita Candelilla Wax | 26 | | | | | 1.95 | |
| Cerabeil White | 2 | | | | | | 1.95 |
| Phase C | | | | | | | |
| Octocrylene | 21 | 2.08 | 2.08 | 2.08 | 2.08 | 2.08 | 2.08 |
| Homosalate | 22 | 2.92 | 2.92 | 2.92 | 2.92 | 2.92 | 2.92 |
| Ethylhexyl salicylate | 23 | 2.08 | 2.08 | 2.08 | 2.08 | 2.08 | 2.08 |
| Phase D | | | | | | | |
| Polyacrylamide and $C_{13}$-$C_{14}$ Isoparaffin and Laureth-7 | 24 | 1.5 | 1.5 | 1.5 | 1.5 | 1.5 | 1.5 |

TABLE 3b-continued

| Ingredient Name | Ingredient | Sample 10 (Ingredient 31) (Quantity %) | Sample 11 (Ingredient 16) (Quantity %) | Sample 12 (Ingredient 12) (Quantity %) | Sample 13 (Glycofilm) (Quantity %) | Sample 14 (Candelilla wax) (Quantity %) | Sample 15 (Beeswax) (Quantity %) |
|---|---|---|---|---|---|---|---|
| Disodium EDTA | 6 | 0.1 | 0.1 | 0.1 | 0.1 | 0.1 | 0.1 |
| Water | 30 | 75.1 | 75.1 | 75.1 | 75.1 | 75.1 | 75.1 |
| Glycerine | 18 | 5 | 5 | 5 | 5 | 5 | 5 |
| Phase E | | | | | | | |
| Phenoxyethanol and ethylhexylglycerin | 17 | 0.8 | 0.8 | 0.8 | 0.8 | 0.8 | 0.8 |
| | | 100.0 | 100.0 | 100.0 | 100.0 | 100.0 | 100.0 |
| Adhesion level (1 = low, 3 = high) | | 2 | 1 | 2 | 2 | 2 | 1 |

Particle adhesion was performed and assessed as detailed above for Example 1. The oil-in-water emulsions were coated as detailed above for Example 1 onto collagen sheets. Particle adhesion was assessed and a visual rating system was used as detailed above for Example 1. The adhesion level of all samples was 2 except Sample 11 which had an adhesion level of 1. The results generally demonstrate that in the O/W chassis, using Ingredient 16 at a ~2% level reduced carbon black particle adhesion compared to the control without any high melting point material (Sample 4) or a number of other high melting point materials (other Samples, Samples 5-10 and 12-15).

Example 3: Preparation of Water-In-Oil Emulsion

Formulations in Samples 16-21 were prepared according to the following procedure. The amounts (quantity percentages) used for each sample are specified in Table 4 below.

Step 1:
All of the Phase A ingredients were mixed together. The Phase A ingredients were stirred with a spatula until homogenous.

Step 2:
The Phase B ingredients were loaded and stirred. Mixing was continued until uniform.

Step 3:
The Phase A mixture was slowly added into the Phase B mixture using a pipette. The mixture was stirred at approximately 700 rpm.

Step 4:
A premix of propylene glycol (Ingredient 25) with preservative (Ingredient 19) was added while mixing. Mixing was conducted at the highest shear using a Silverson mixer for 1 minute intervals until uniform water-in-oil emulsions were formed. If the product already had a thick, creamy consistency, then mixing using a Silverson mixer was not needed.

TABLE 4

| Ingredient Name | Ingredient | Sample 16 (Control Formula) (Quantity %) | Sample 17 (Ingredient 9) (Quantity %) | Sample 18 (Ingredient 8) (Quantity %) | Sample 19 (Ingredient 14) (Quantity %) | Sample 20 (Ingredient 32) (Quantity %) | Sample 21 (Ingredient 16) (Quantity %) |
|---|---|---|---|---|---|---|---|
| Phase A | | | | | | | |
| Water | 30 | 72.2 | 72 | 72 | 72 | 72 | 72 |
| Sodium Chloride | 27 | 1 | 1 | 1 | 1 | 1 | 1 |
| Glycerine | 18 | 5 | 5 | 5 | 5 | 5 | 5 |
| Phase B | | | | | | | |
| Isododecane and polypropylsilsesquioxane | 8 | — | — | 2.6 | — | — | — |
| Isododecane and acrylates/polytrimethylsiloxymethacrylate copolymer | 9 | — | 5 | — | — | — | — |
| Dimethicone | 31 | — | 5 | — | — | 8.05 | — |
| Trimethylsiloxysilicate and polypropylsilsesquioxane | 14 | — | — | — | 1.95 | — | — |
| Dimethicone | 32 | — | — | — | — | 1.95 | — |
| $C_{30}$-$C_{45}$ Alkyldimethylsilyl polypropylsilsesquioxane | 16 | — | — | — | — | — | 1.95 |
| Lauryl PEG-10 tris(trimethylsiloxy)silylethyl dimethicone | 7 | 2 | 2 | 2 | 2 | 2 | 2 |
| Isododecane | 8 | 11.8 | 1.8 | 9.2 | 9.85 | 1.8 | 9.85 |
| Mineral oil | 20 | 3 | 3 | 3 | 3 | 3 | 3 |
| $C_{12}$-$C_{15}$ Alkyl Benzoate | 5 | 3 | 3 | 3 | 3 | 3 | 3 |
| Phase C | | | | | | | |
| Diazolidinyl urea and iodopropynyl butylcarbamate | 19 | 0.5 | 0.5 | 0.5 | 0.5 | 0.5 | 0.5 |
| Propylene Glycol | 25 | 1.5 | 1.5 | 1.5 | 1.5 | 1.5 | 1.5 |
| | | 100 | 89.8 | 92.4 | 89.8 | 89.8 | 100 |
| Adhesion level (1 = low, 3 = high) | | 3 | 2 | 3 | 3 | 3 | 3 |

Particle adhesion was performed and assessed as detailed above for Example 1. The water-in-oil emulsions were coated as detailed above for Example 1 onto collagen sheets. Particle adhesion was assessed and a visual rating system was used as detailed above for Example 1. The adhesion level of all samples was 3 except Sample 17 which had an adhesion level of 2. The results generally demonstrate that in the W/O chassis, using Ingredient 9 at a ~2% level reduced carbon black particle adhesion compared to the control without any high melting point material (Sample 16) or polydimethylsiloxane (Sample 20) or another high melting point material (Samples 18, 19, 21).

Figure 2:
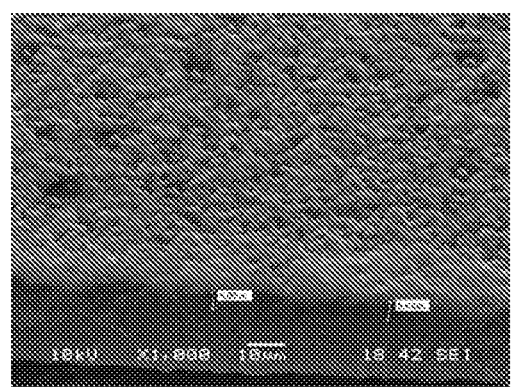
Figure 3:
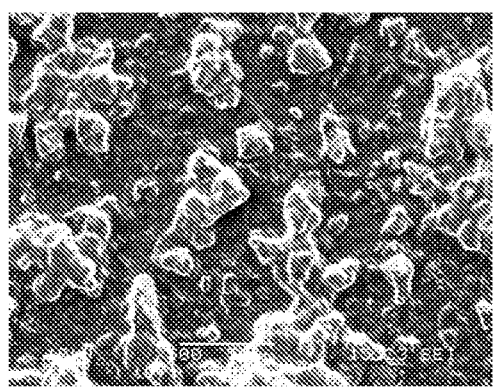

The Scanning Electron Microscopy pictures illustrate surface topography for Samples 16 (FIG. 1), 17 (FIG. 2) and 21 (FIG. 3), before exposition to carbon black particles. For Sample 16 (see FIG. 1), no peaks or valleys were visible and the surface was smooth. As a consequence, there was a large area of contact between the film and the unwanted particles, leading to an observed high adhesion. For Sample 21 (see FIG. 3), the peaks were separated from one another by large distances (order of magnitude of 10 microns and larger). The valleys were large enough so that unwanted particles fit into those and adhered to the film. For Sample 17 (see FIG. 2), peaks and valleys were also visible; however, the peaks were more homogeneously distributed and the valley typical size was smaller (order of magnitude of 1 micron and smaller). The valley size was too small to permit adherence of unwanted particles. The smaller area of contact for Sample 17 led to an observed reduction in adhesion. These results generally demonstrate that using specific high melting point materials in specific cosmetic compositions created a micro-roughness structure providing pollution particle anti-adhesion benefits. Where a homogenous peak-and-valley pattern combined with an inter-peak size in the order of magnitude of 1 micron, the detrimental effects of unwanted particles on skin were expected to be reduced as a consequence of the reduced adhesion level observed.

While the invention is susceptible to various modifications and alternative forms, specific embodiments have been shown by way of example in the drawings and described in detail herein. It should be understood, however, that the invention is not intended to be limited to the particular forms disclosed. Rather, the invention is to cover all modifications, equivalents, and alternatives falling within the spirit and scope of the invention as defined by the appended claims.

What is claimed is:

1. A composition for topical application to the skin of a mammal comprising:
    (a) a hydrophobic non-volatile solvent;
    (b) a hydrophobic non-volatile high melting point material, wherein the hydrophobic non-volatile high melting point material has a melting point in the range of 60° C. and 100° C., wherein the hydrophobic non-volatile high melting point material comprises an acrylic copolymer with dendrimeric silicone groups comprising an acrylates/polytrimethylsiloxymethacrylate copolymer; and
    (c) a hydrophobic volatile solvent comprising isododecane, wherein the hydrophobic volatile solvent compatibilizes the hydrophobic non-volatile solvent and the hydrophobic non-volatile high melting point material; and
    wherein the hydrophobic non-volatile high melting point material is selected to be at least partially incompatible with the hydrophobic non-volatile solvent in the absence of the hydrophobic volatile solvent, where the acrylates/polytrimethylsiloxymethacrylate copolymer and isododecane are present in an amount of at least 5 weight % of the composition.

2. The composition of claim 1, further comprising (d) water and (e) one or more emulsifying systems, the composition being in a form of an oil-in-water emulsion, a water-in-oil emulsion, or a hydrogel, wherein the non-volatile high melting point material is selected to be at least partially incompatible with the hydrophobic non-volatile solvent and the one or more emulsifying systems in the absence of the hydrophobic volatile solvent.

3. The composition according to claim 1, wherein the hydrophobic non-volatile solvent is selected from hydrocarbon oils of animal origin, hydrocarbon oils of vegetable origin, linear and branched hydrocarbons of mineral and synthetic origin, synthetic ethers comprising from 10 to 40 carbon atoms, synthetic esters, fatty alcohols that are liquid at ambient temperature and that comprise a branched and/or unsaturated carbon chain comprising from 12 to 26 carbon atoms, linear polydimethylsiloxanes, branched polydimethylsiloxanes, polydimethylsiloxanes substituted with fluoro, hydroxyl, thiol, amine, aliphatic, aromatic, polyoxyalkylene groups, fatty acids, fatty alcohols, sunfilters, or any combination thereof.

4. The composition according to claim 1, wherein the hydrophobic non-volatile high melting point material is characterized by having an amorphous phase, a crystalline phase, or a combination of an amorphous phase and a crystalline phase at 25° C. and atmospheric pressure conditions.

5. The composition according to claim 1, wherein the hydrophobic non-volatile high melting point material has a melting point in the range of 60° C. and 90° C.

6. The composition of claim 2, wherein the one or more emulsifying systems are selected from PEG, PEG/PPG or polyglycerin modified dimethicone, alkyldimethicone, dimethicone crosspolymer or ABn copolymer derivatives, fatty acid esters of polyols, polyoxyethylenated fatty acid esters of sorbitol; polyoxyethylenated alkyl ethers, carboxylates, amino acid derivatives, alkyl sulfates, alkyl ether sulfates and oxyethylenated derivatives thereof, sulfonates, isethionates, N-acylisethionates, taurates, N-acyl N-methyltaurates, sulfosuccinates, alkylsulfoacetates, phosphates, alkyl phosphates, polypeptides, anionic derivatives of alkyl polyglycoside, fatty acid soaps, polymeric o/w emulsifiers, or any combination thereof.

7. The composition according to claim 1, further comprising one or more ingredients selected from humectants, emollients, exfoliate agents, vitamins and their derivatives, natural extracts and their derivatives, anti-oxidants, radical scavengers, anti-acne agents, anti-inflammatory agents, anti-microbial agents, antibacterial agents, antifungal agents, anti-itch agents, peptides, proteins, sunscreens, sunfilters, skin lightening agents, tanning agents, drugs, pigments, dyes, electrolytes, sequestrants, anhydrous liquids, thickeners/rheology modifiers, preservatives, fragrances, pH modifiers, and combination(s) thereof.

8. The composition according to claim 1, the composition being configured to create a film having micro-roughness when applied onto skin or a collagen sheet and having a non-smooth surface on scanning electron microscopy images with magnification ×1,000.

9. The composition according to claim 1, wherein the composition is present in a skin care or cosmetic product in a form selected from lotions, creams, moisturizers, facial treatments, primers, concealers, foundations, make-ups, color cosmetics, blushes, lipsticks, lip balms, eyeliners, powders, and sunscreens.

10. A method of preparing a composition for topical application to the skin of a mammal, comprising the steps of mixing:
(a) a hydrophobic non-volatile solvent;
(b) a hydrophobic non-volatile high melting point material, wherein the hydrophobic non-volatile high melting point material has a melting point in the range of 60° C. and 100° C., wherein the hydrophobic non-volatile high melting point material comprises an acrylic copolymer with dendrimeric silicone groups comprising an acrylates/polytrimethylsiloxymethacrylate copolymer; and
(c) a hydrophobic volatile solvent comprising isododecane, wherein the hydrophobic volatile solvent compatibilizes the hydrophobic non-volatile solvent and the hydrophobic non-volatile high melting point material; and
wherein the hydrophobic non-volatile high melting point material is selected to be at least partially incompatible with the hydrophobic non-volatile solvent in the absence of the hydrophobic volatile solvent,
where the acrylates/polytrimethylsiloxymethacrylate copolymer and isododecane are present in an amount of at least 5 weight % of the composition.

11. The method of claim 10, further comprising mixing (d) water and (e) one or more emulsifying systems with the hydrophobic non-volatile solvent, the hydrophobic non-volatile high melting point material, and the hydrophobic volatile solvent into an oil-in-water emulsion, a water-in-oil emulsion, or a hydrogel, wherein the non-volatile high melting point material is selected to be at least partially incompatible with the hydrophobic non-volatile solvent and the one or more emulsifying systems in the absence of the hydrophobic volatile solvent.

12. A method for forming a protective film on the skin of a mammal, comprising topically administering to the skin a composition comprising:
(a) a hydrophobic non-volatile solvent;
(b) a hydrophobic non-volatile high melting point material, wherein the hydrophobic non-volatile high melting point material has a melting point in the range of 60° C. and 100° C., wherein the hydrophobic non-volatile high melting point material comprises an acrylic copolymer with dendrimeric silicone groups comprising an acrylates/polytrimethylsiloxymethacrylate copolymer; and
(c) a hydrophobic volatile solvent comprising isododecane, wherein the hydrophobic volatile solvent compatibilizes the hydrophobic non-volatile solvent and the hydrophobic non-volatile high melting point material; and
wherein the non-volatile high melting point material is selected to be at least partially incompatible with the hydrophobic non-volatile solvent and the one or more emulsifying systems in the absence of the hydrophobic volatile solvent; and
where the acrylates/polytrimethylsiloxymethacrylate copolymer and isododecane are present in an amount of at least 5 weight % of the composition, and wherein the composition creates a protective film on the skin that minimizes adhesion of unwanted particles.

13. The method of claim 12, wherein the composition further comprises (d) water and (e) one or more emulsifying systems, the composition being in a form of an oil-in-water emulsion, a water-in-oil emulsion, or a hydrogel, wherein the non-volatile high melting point material is selected to be at least partially incompatible with the hydrophobic non-volatile solvent and the one or more emulsifying systems in the absence of the hydrophobic volatile solvent.

14. The method of claim 12, wherein the hydrophobic non-volatile solvent is selected from hydrocarbon oils of animal origin, hydrocarbon oils of vegetable origin, linear and branched hydrocarbons of mineral and synthetic origin, synthetic ethers comprising from 10 to 40 carbon atoms, synthetic esters, fatty alcohols that are liquid at ambient temperature and that comprise a branched and/or unsaturated carbon chain comprising from 12 to 26 carbon atoms, linear polydimethylsiloxanes, branched polydimethylsiloxanes, polydimethylsiloxanes substituted with fluoro, hydroxyl, thiol, amine, aliphatic, aromatic, polyoxyalkylene groups, fatty acids, fatty alcohols, sunfilters, or any combination thereof.

15. The method of claim 12, wherein the one or more emulsifying systems are selected from PEG, PEG/PPG or polyglycerin modified dimethicone, alkyldimethicone or dimethicone crosspolymer derivatives, fatty acid esters of polyols, polyoxyethylenated fatty acid esters of sorbitol; polyoxyethylenated alkyl ethers, carboxylates, amino acid derivatives, alkyl sulfates, alkyl ether sulfates and oxyethylenated derivatives thereof, sulfonates, isethionates, N-acylisethionates, taurates, N-acyl N-methyltaurates, sulfosuccinates, alkylsulfoacetates, phosphates, alkyl phosphates, polypeptides, anionic derivatives of alkyl polyglycoside, fatty acid soaps, polymeric o/w emulsifiers, or any combination thereof.

16. The method of claim 12, further comprising evaporating or vaporizing the hydrophobic volatile solvent.

17. The method of claim 12, where the method provides a homogenous peak-and-valley pattern combined with an inter-peak size in the order of magnitude of 1 micron as measured by scanning electron microscopy.

18. The composition of claim 1, where the composition provides a homogenous peak-and-valley pattern combined with an inter-peak size in the order of magnitude of 1 micron as measured by scanning electron microscopy after coating the composition on a collagen sheet and allowing the composition to dry.

* * * * *